United States Patent [19]
Hagino et al.

[11] 4,327,042
[45] Apr. 27, 1982

[54] DRAFT DEVICE FOR A BUBBLE COLUMN

[75] Inventors: Hiroshi Hagino, Tokyo; Hideo Odagiri; Junichi Okutani, both of Hofu, all of Japan

[73] Assignee: Kyowa Hakko Kogyo Co., Ltd., Tokyo, Japan

[21] Appl. No.: 218,774

[22] Filed: Dec. 22, 1980

[30] Foreign Application Priority Data

Dec. 25, 1979 [JP] Japan .................. 54-167667

[51] Int. Cl.³ .......................................... F02M 17/20
[52] U.S. Cl. ................................. 261/77; 435/314; 435/818; 210/205
[58] Field of Search .............. 261/77; 435/313, 314, 435/315, 316, 818; 210/205

[56] References Cited

U.S. PATENT DOCUMENTS

| 1,937,434 | 11/1933 | Piatt | 438/818 X |
| 3,236,744 | 2/1966 | Yamaha | 435/314 |
| 3,400,051 | 9/1968 | Hofschneider | 435/314 |
| 3,852,384 | 12/1974 | Bearden | 261/77 |
| 3,969,446 | 7/1976 | Franklin, Jr. | 261/77 |

FOREIGN PATENT DOCUMENTS

| 1172674 | 1/1965 | Fed. Rep. of Germany . |
| 1196165 | 7/1965 | Fed. Rep. of Germany . |
| 2753388 | 7/1978 | Fed. Rep. of Germany . |
| 1238663 | 7/1960 | France . |
| 2073933 | 10/1971 | France . |
| 2281980 | 3/1976 | France . |
| 1123546 | 8/1968 | United Kingdom . |
| 396361 | 1/1974 | U.S.S.R. . |

Primary Examiner—Robert J. Warden
Attorney, Agent, or Firm—Fitzpatrick, Cella, Harper & Scinto

[57] ABSTRACT

Disclosed is an improved draft device for a bubble column used in a reaction wherein gas and liquid are mixed such as fermentation. The draft device consists of a plurality of vertical plates coaxially arranged within the bubble column such that each plate has one vertical edge in outwardly spaced overlapping relation to a vertical edge of an adjacent plate and has the other vertical edge in inwardly spaced overlapping relation to a vertical edge of the other adjacent plate.

7 Claims, 3 Drawing Figures

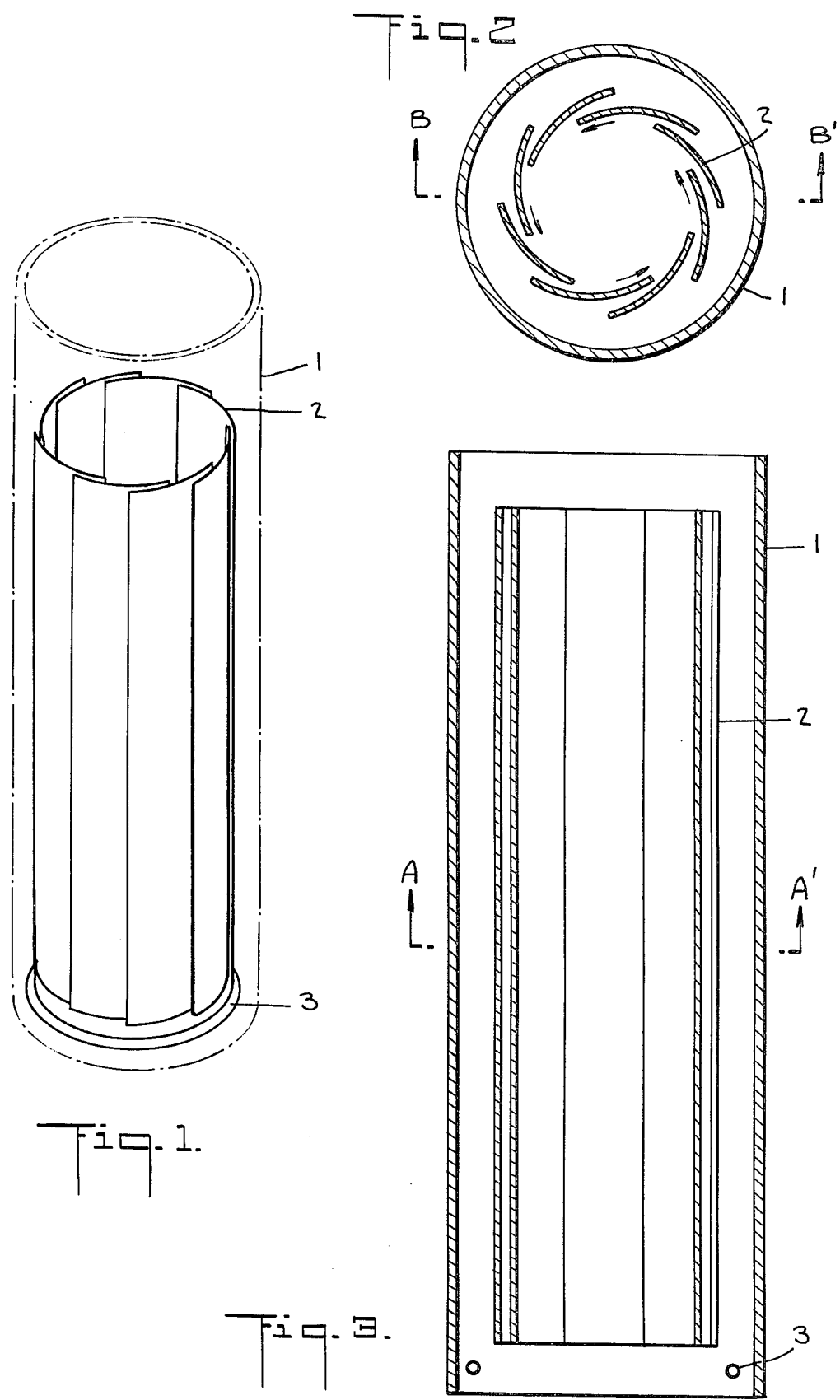

DRAFT DEVICE FOR A BUBBLE COLUMN

BACKGROUND OF THE INVENTION

The present invention relates generally to a draft device for a bubble column and, more specifically a bubble column having plural plates. A bubble column is a reaction vessel which is generally used for a reaction wherein gas and liquid are mixed, particularly for fermentation, and which is supplied at its bottom with a gas such as air for causing agitation therein.

A bubble column has a number of advantages over a reaction vessel having an agitator, such as lower cost of installation, easier maintenance and a higher efficiency of agitation per unit power. However, disadvantageously, the liquid in the column is circulated at a low rate, and the bubbles formed in the column are difficult to remove.

As an improved bubble column, there has been proposed a bubble column having a draft tube of cylindrical construction which is coaxial with the column, as disclosed in Japanese Published Unexamined Patent Application No. 99380/1973. In such device, either the outside or inside of the draft tube is aerated or supplied with a gas, and after the gas is caused to flow upward in the aerated area, it flows downward through the non-aerated area, so that the agitation of the liquid in the column may be enhanced. The formed bubbles are entrained in the down flow and disappear.

However, in some reaction procedures, it is necessary to supply a large quantity of culture medium as the reaction proceeds. When a bubble column is used for such reaction, the level of the liquid in the column changes as its quantity increases. For reactions of this type, there has been proposed a bubble column having a draft tube of which the height is adjustable to maintain the same effect of agitation when the quantity of the liquid in the column is changed as is disclosed in Japanese Published Unexamined Patent Application No. 55780/1979. In this known device, a complicated arrangement is, however, required for varying the height of the draft tube during the reaction. It is, therefore, desirable to develop a simple device which provides an effective liquid circulation in a bubble column. To this end, it has been found that a draft device having a plurality of plates provided in a bubble column enables efficient circulation of the liquid in the column and substantial gas flow entraining bubbles in addition to the above-mentioned effect of a draft tube.

SUMMARY OF THE INVENTION

In accordance with the present invention, there is provided a bubble column having a draft device comprising a plurality of coaxially disposed plates wherein each plate has one vertical edge in outwardly spaced, overlapping relation to a vertical edge of an adjacent plate, and the other vertical edge in inwardly spaced, overlapping relation to the vertical edge of the other adjacent plate.

There has thus been broadly outlined the more important features of the invention in order that the detailed description thereof that follows may be better understood and in order that the present contribution to the art may be better appreciated. There are, of course, additional features of the invention that will be described hereinafter and which will form the subject of the claims appended hereto. Those skilled in the art will appreciate that this invention may be utilized as the basis for designing other applications for carrying out the purposes thereof. It is, therefore, important that the claims be regarded as including such equivalent embodiments as do not depart from the spirit and scope of the invention.

BRIEF DESCRIPTION OF THE DRAWINGS

One embodiment of the invention has been chosen for purposes of illustration and description, and is shown in the accompanying drawings, forming a part of the specification, wherein:

FIG. 1 is a perspective view of draft device of the invention as provided in a bubble column;

FIG. 2 is a transverse sectional view taken along the line A-A' of FIG. 3, in which the arrows show the direction of flow of the liquid; and FIG. 3 is a longitudinal sectional view taken along the line B-B' of FIG. 2.

DETAILED DESCRIPTION OF THE INVENTION

The draft device of the present invention comprises a plurality of plates 2 coaxially disposed in a bubble column 1 which is provided at the bottom with an aeration pipe 3.

The size and form of the draft device of the present invention may be varied depending on the size of the bubble column and the kind of the reaction. It generally comprises 2 to 30 plates 2, and preferably 4 to 16 plates 2. As for the height, it is desirable that the upper ends of plates 2 are slightly below the level of the liquid in the column when the supply of gas is off. The plates overlap each other so that the total surface area of all the plates will be 1 to 4 times as large as the apparent surface area of the draft device. The space between the face of a plate and an adjacent plate is variable according to the viscosity of the culture liquor and diameter of column 1. Usually the space between overlapping faces is 1 to 25 cm.

Plates 2 may be square, rectangular, rhombic, trapezoidal, or of any other appropriate shape. The cross-sectional configuration of each plate, may have the form of a straight, curved or bent line, or a combination thereof. As is illustrated in FIG. 2, however, it is preferable that the transverse cross-section of each plate 2 is a curved line and most preferably an arc of a circle. In this regard, the curvature of the arcs is preferably between that of the circle of the column 1 and that of the apparent circle formed by the plates 2 when the centers of the arcs are on the circumference. The diameter of the apparent circle of the plates 2 is generally 0.65 to 0.75 that of the diameter of column 1.

Plates 2 may have a hollow box-like structure, and the thickness of the plates is not critical and thus need not be uniform. Plates 2 may be constructed of various materials depending on the kind of the reaction to be carried out in the bubble column. Generally, those materials usually used for forming the inner surface of a reaction vessel, including iron, stainless steel and plastics may be utilized.

The plates can be fixed in the column as baffle plates are usually mounted in a vessel. While the draft device generally has a cylindrical shape which is coaxial with the bubble column, it may also form a frustum having an open top, or a combination of a cylinder and a frustum. The draft device of this invention may also be used in combination with a known draft tube or in the form of two or more units disposed one above another.

Excellent effects can be attained by using the present device. For example, it has a high bubble breaking effect owing to a powerful flow of entrainment of the liquid in the column; and it is simple in construction, and does not require any operation outside the device.

The flow and agitation of the fluid in the bubble column provided with the present draft device may be generally described as follows. When air is introduced into the column through an aeration pipe 3 provided at the bottom thereof in the region between the draft device and the column (hereinafter referred to as the 'outer periphery'), an upward flow of the liquid occurs along the outer periphery of the device, while a downward flow of the liquid occurs inside the device. A portion of the liquid flowing along the outer periphery enters the draft device through the spaces between the plates 2. The device has a function of separating its internal and external spaces from each other, and thereby produces the draft effect. When the liquid flows into the draft device through the spaces between the plates 2, it is given a force of rotation about the center of the device as it is guided along the inner surfaces of the plates 2, so that a gyrating flow of the liquid is formed as is illustrated by the arrows in FIG. 2.

As the liquid approaches the inner wall of the column 1, it tends to rise due to the centrifugal force. This effect, in combination with the pressure drop of the liquid flowing through the spaces between the plates, and upward movement of the gas, creates a swirling action. The swirl prevents flow of the liquid toward the center of the draft device in the lower portion thereof, and promotes liquid flow toward the center on the surface thereof. The swirl also entrains the bubbles formed on the surface of the liquid, and the bubbles are broken very effectively thus promoting entrainment and agitation.

A bubble column provided with the draft device of the present invention is advantageously used in any reaction wherein gas and liquid are mixed, especially in liquid fermentation using an aerobic microorganism. For example, the bubble column is used in the liquid fermentation for producing amino acids, organic acids, nucleic acids, antibiotics, enzymes, etc..

Certain specific applications of the present invention are illustrated in the following representative examples.

EXAMPLE 1

In this example, *Corynebacterium glutamicum* ATCC 21543 is inoculated into a 2L-Erlenmeyer flask containing 300 ml of seed medium (pH 7.3) comprising 40 g/L glucose, 2 g/L $KH_2PO_4$, 0.5 g/L $MgSO_4.7H_2O$, 10 mg/L $MnSO_4.4H_2O$, 10 mg/L $FeSO_4.7H_2O$, 50 µg/L biotin, 100 µg/L thiamine hydrochloride, 50 ml/L hydrolyzate of soybean meal and 3 g/L urea and cultured at 30° C. for 24 hours with shaking.

Then, 3 L of the thus obtained seed culture is transferred into a 300 L-fermenter containing 150 L of a medium having the same composition as the seed medium and cultured at 30° C. for 24 hours with aeration and agitation.

Of the thus obtained second seed culture 120 L is transferred into a fermenter provided with an agitator and an equal amount is also transferred into a bubble column, each containing 1.2 kl of fermentation medium (pH 7.5) comprising 160 g/L glucose, 0.5 g/L $KH_2PO_4$, 0.5 g/L $MgSO_4.7H_2O$, 10 mg/L $FeSO_4.7H_2O$, 50 µg/L biotin, 100 µg/L thiamine hydrochloride and 10 ml/L hydrolyzate of soybean meal. Culturing is carried out under conditions indicated in Table 1. The pH of the culture is controlled at 7.0 with ammonia gas. The specifications of the fermenter and the bubble column are as follows.

Bubble column
  Diameter: 80 cm
  Height: 4 m
Draft device
  Diameter: 56 cm
  Height: 3 m
  Number of plates: 4
  Size of each plate: 3 m×50 cm
  Spacing between plates: 1 cm
  Curvature of plate: the same as that of column
Fermenter
  Diameter: 1.2 m
  Height: 1.8 m

TABLE 1

|  | Bubble column | Fermenter |
|---|---|---|
| Culturing condition |  |  |
| Temperature (°C.) | 30 | 30 |
| Culturing period (Hr) | 30 | 39 |
| Aeration (N m³/min) | 2.0 | 1.2 |
| Agitation (r.p.m.) | — | 130 |
| Concentration of cells (g/L) | 20 | 22 |
| Yield of lysine (HCl) (g/L) | 54.2 | 49.2 |

EXAMPLE 2

In this example, the same strain, bubble column and fermenter as in Example 1 are used and the same procedures as in Example 1 are repeated except that 160 g/L cane blackstrap molasses (as glucose) is used instead of glucose in the fermentation medium. The results are shown in Table 2.

TABLE 2

|  | Bubble column | Fermenter |
|---|---|---|
| Culturing period (Hr) | 32 | 40 |
| Concentration of cells (g/L) | 20.5 | 21.0 |
| Yield of lysine (HCl) (g/L) | 53.9 | 48.4 |

What is claimed is:

1. In a bubble column for reactions wherein gas and liquid are mixed comprising a cylindrical vertically disposed column and means for introducing a gas to the bottom of said column, an improved draft device which comprises a plurality of plates coaxially disposed within said column; each of said plates having one vertical edge in outwardly spaced, overlapping relation to a vertical edge of adjacent plate, and the other vertical edge in inwardly spaced, overlapping relation to a vertical edge of the other adjacent plate.

2. An improved draft device according to claim 1 wherein said plates are disposed whereby said overlap provides a total surface area of the plates of 1 to 4 times the apparent surface area of the draft device.

3. An improved draft device according to claim 1 wherein said plates are arcuate in transverse cross-section.

4. An improved draft device according to claim 1 wherein said plates are vertically disposed within said column.

5. An improved draft device according to claim 4 wherein said plates are arcuate in transverse cross-section.

6. An improved draft device according to claim 5 wherein the centers of the arcs of said plates define a circle which is 0.65 to 0.75 that of the diameter of said column.

7. An improved draft device according to claim 1 wherein said plates are disposed within said column as a frustrum.

* * * * *